United States Patent [19]

Ring

[11] 4,291,696

[45] Sep. 29, 1981

[54] COMPACT TAMPON-APPLICATOR ASSEMBLY WITH RIBBED INNER TUBE

[75] Inventor: David F. Ring, Morganville, N.J.

[73] Assignee: Johnson & Johnson Products, Inc., New Brunswick, N.J.

[21] Appl. No.: 79,612

[22] Filed: Sep. 27, 1979

[51] Int. Cl.³ ............................................. A61F 15/00
[52] U.S. Cl. .................................................... 128/263
[58] Field of Search ....................... 128/263, 285, 270

[56] References Cited

U.S. PATENT DOCUMENTS

| | | | |
|---|---|---|---|
| 2,829,646 | 4/1958 | Kurkjian | 128/263 |
| 2,832,342 | 4/1958 | Wingenroth | 128/263 |
| 3,101,713 | 8/1963 | Sargent | 128/263 |
| 4,048,998 | 9/1977 | Nigro | 128/263 |

Primary Examiner—John D. Yasko
Attorney, Agent, or Firm—Jason Lipow

[57] ABSTRACT

A tampon-applicator assembly of reduced length is provided consisting of a cylindrical outer tube and a cylindrical inner tube snuggly nested coaxially within said outer tube. The inner tube is provided with a plurality of radially spaced ribs extending longitudinally along the inside surface thereof, the ribs terminating in bearing surfaces. A tampon is coaxially enclosed within the inner tube. A gripping portion is affixed to the distal end of the inner tube and extends out of the distal end of the outer tube. The gripping portion is provided for gripping the inner tube and reciprocating the same almost completely out of the distal end of the outer tube. At least one restraining element is provided in the distal end of the outer tube for restraining the tampon from reciprocating with the inner tube. In operation, the inner tube is reciprocated in a distal direction and the tampon is transferred from the inner tube to the outer tube. To insert the tampon, the inner tube is then reciprocated in the proximal direction and the ribs will bear against the distal end of the tampon and expel the same from the outer tube.

4 Claims, 5 Drawing Figures

U.S. Patent     Sep. 29, 1981     4,291,696
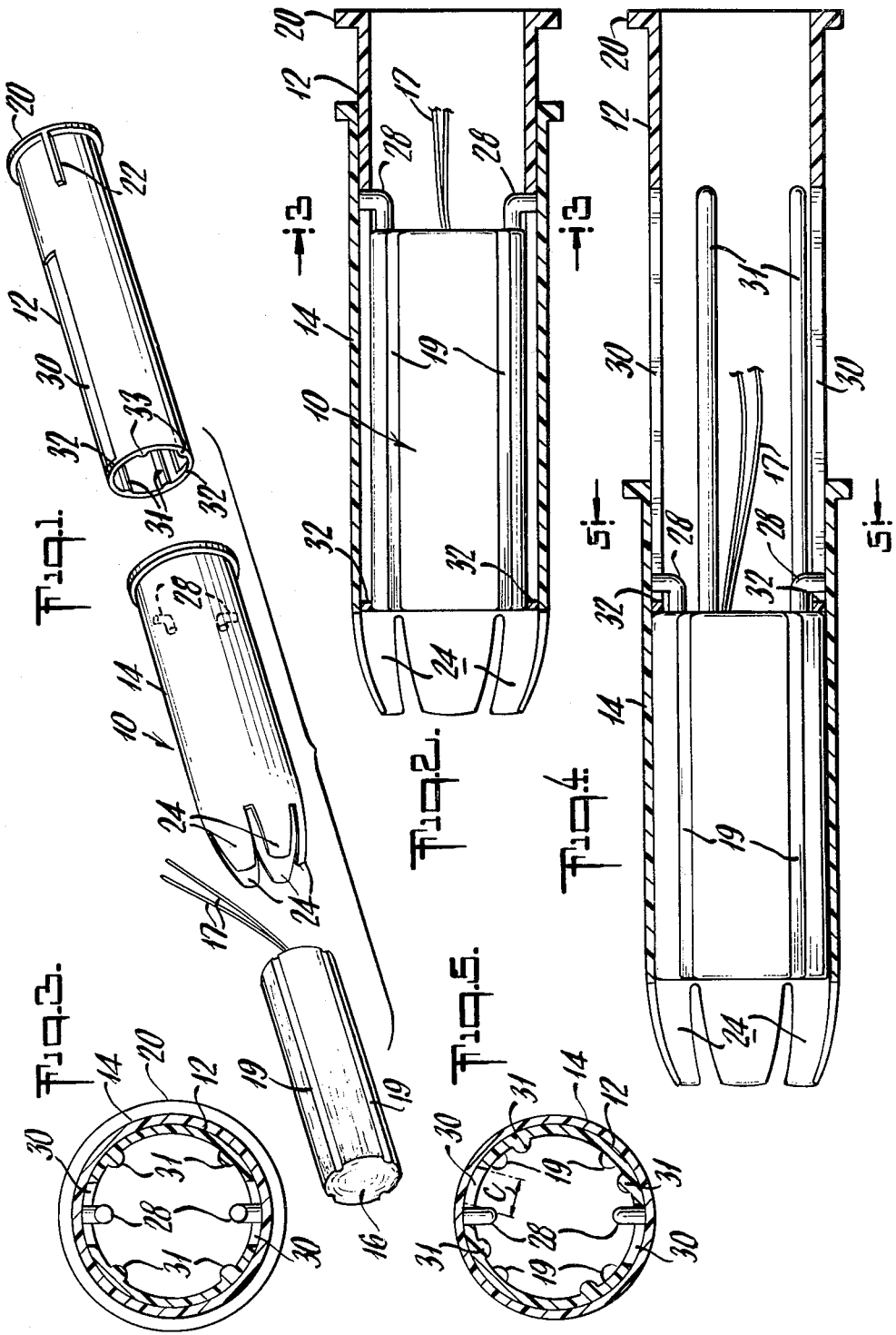

COMPACT TAMPON-APPLICATOR ASSEMBLY WITH RIBBED INNER TUBE

BACKGROUND OF THE INVENTION

This invention relates to tampon-applicator assemblies and is particularly directed toward such assemblies provided in a compact, unobtrusive, conveniently short form.

Many applicators for introducing catamenial tampons intervaginally have been suggested in the art and several are now on the market. The kind in widest use comprises an open ended tubular holder containing the tampon and is combined with a plunger adapted to slideably expel the tampon from the holder. The plunger is also generally tubular, though smaller in diameter than the holder, and is telescopically positioned therein so that by moving the plunger into one end of the holder, the tampon may be ejected from the opposite end. The holder is, of necessity, longer than the tampon and, to insure complete ejection of the tampon from the holder, the plunger is generally longer than the holder. Consequently, the overall length of the holder and plunger assembly is always more than twice the length of the tampon.

Several drawbacks are associated with such prior tampon-applicator assemblies. To provide sufficient assemblies for a menstrual period, it is customary to package a number of these, e.g., ten, in a single container. From the foregoing description, it is apparent that the tampon applicators and hence the containers used to package them are comparatively large with respect to the article, i.e., the tampon, ultimately used by the consumer. The necessity for large containers greatly adds to the cost of the marketed product, such added cost being particularly important in products of the kind herein considered, i.e., products intended for a single use and thereafter discarded. Accordingly, there is an economic incentive for a reduction in product size.

Perhaps even more importantly, a size reduction is advantageous from both a convenience and an aesthetic point of view. Firstly, the product should be small enough to be conveniently carried in a woman's purse. Secondly, from an aesthetic viewpoint, a shorter more compact product is less noticeable and hence less embarrassing.

The prior art now abounds with suggestions of prior investigators for avoiding this problem of excessive length. I believe that none of these prior suggestions has reached commercial fruition primarily because of shortcomings in such design which add cost, complexity or functional inconvenience to the product.

In a series of prior art suggestions (see for example, U.S. Pat. Nos. 3,115,876; 3,424,159; 3,059,642; 3,034,508; 3,103,929; 3,831,605; 3,090,385) it has been suggested that the plunger and holder be provided in assembled form or hinged together so that they may be packaged side by side, thereby substantially reducing the overall length of the packed tampon-applicator assembly. Such designs have not met with commercial success and, it is believed that this is because, in addition to the complexity and expense in manufacturing the products the user does not wish to be faced with the added operation of reassembling the plunger/holder combination into the operable configuration.

Another approach to a solution for the problem of excessive length is exemplified by U.S. Patent Application Ser. No. 833,201, filed on Sept. 14, 1977, by Michael Loyer. In accordance with this method, the tampon enclosed or partially enclosed within a holder is provided with an inner, axially extending bore in which the plunger resides prior to use. In use, the plunger is first pulled or screwed out of the bore, then locked in place and reciprocated toward the tampon to eject the same from the holder. While the operation of this kind of applicator assembly is relatively simple, unfortunately the concept involves a specially designed tampon having the required inner bore. Both because of the added difficulty of manufacturing such a tampon at high speed and because of the disadvantageous functional consequences resulting from a tampon of this kind, the solution suggested by Loyer has not been satisfactory.

Still another suggestion for solving the excessive length problem is exemplified by U.S. Pat. Nos. 2,832,342 and 3,101,713. This concept involves providing a tampon applicator assembly comprising two concentric tubes, providing one such tube nested within the other, and having the tampon provided within the inner tube. The inner tube is then reciprocated axially almost completely out of the outer tube and means are provided for preventing the tampon from being reciprocated along with the inner tube. Accordingly, when the inner tube is in its reciprocated position, the tampon now resides within the outer tube and along side the inner tube. The inner tube is then reciprocated toward the tampon and hence acts as a plunger for expelling the tampon from the remote end of the outer tube.

The problem with this suggestion is that in order for the inner tube to act as a plunger, the inner tube must in some way bear against the tampon. In both of the above-described patents, this is accomplished by selecting a tampon and sizing the diameters and thicknesses of the inner and outer tubes in such manner that when the tampon is transferred from the inner tube to the outer tube, the tampon expands in diameter to fill the outer tube. Accordingly, with the tampon now having a diameter equal to the inside diameter of the outer tube and also equal to the outside diameter of the inner tube, the walls of the inner tube will bear against the peripheral portions of the end of the tampon during the expulsion step.

There are several drawbacks encounted by this technique of obtaining bearing surface for the plunger. Firstly, the method is only applicable to relatively resiliently compressed tampons. In contrast thereto, the highly compressed cellulosic tampons do not generally have the resiliency to spring back and fill the outer tube upon being released from the inner tube. Secondly, the necessity of providing the tampon in a resilient compressed state also implies that the tampon in the packed state will be exerting pressure on the walls of the inner tube and, after this inner tube is retracted, on the walls of the outer tube. This pressure substantially increases the frictional resistance generated between the walls of the respective tubes and the tampon when retracting the tampon from the inner tube and expelling the tampon from the outer tube. It is highly undesirable to have any substantial resistance to these operations and, in fact, the frictional resistance should ideally be no more than is required for holding the tampon within the applicator assembly prior to use.

In view of the above, no completely satisfactory system has heretofore been devised for solving the excessive length problem.

SUMMARY OF THE INVENTION

In accordance with this invention, a tampon-applicator assembly is provided which overcomes the shortcomings of the art and provides such assembly in reduced length form without increased expense in manufacturing or increased inconvenience in use.

Specifically, a tampon-applicator assembly is provided having a proximal end and a distal end. As used herein, the term "proximal end" is meant to describe those portions of the assembly and its parts which are closest to the user's body when the tampon is emplaced within the vagina. The term "distal end" is meant to describe those portions of the assembly and its parts that are most remote from the body when the tampon is being emplaced.

The assembly comprises a generally cylindrical outer tube and a generally cylindrical inner tube. The inner tube has an outside diameter that is slightly less than the inside diameter of the outer tube and is snuggly nested and coaxially aligned within the outer tube. A tampon is provided, enclosed and coaxially aligned within the inner tube. It is preferred that the inner and outer tubes are both of approximately the same length and that such length is only slightly longer than the length of the tampon. Thus when the two tubes are nested and the tampon is enclosed within the inner tube, the entire assembly, now in the configuration presented to the user prior to use, will be only slightly longer than the tampon.

The distal end of the inner tube is provided with a gripping portion which extends out of the distal end of the outer tube when the inner tube is nested therein. The gripping portion is adapted to be gripped by the user to reciprocate the inner tube almost completely out of the distal end of the outer tube thereby placing the assembly into the tampon insertion position. This gripping portion, for example, may be merely a extended part of the inner tube or, alternatively, may be a flange on the distal end of the inner tube, a tab extending from the inner tube or any other of such similar elements as will occur to one skilled in the art.

At least one restraining element is provided in the outer tube and, specifically, in the distal half of the inside wall of the outer tube. The restraining element is adapted to bear against the distal end of the tampon and prevent the tampon from moving together with the inner tube, when the inner tube is reciprocated into the insertion position. Accordingly, when the inner tube is so reciprocated and the tampon restrained, the tampon will effectively transfer from a position of being immediately enclosed by the inner tube to the position of being immediately enclosed by the outer tube.

The restraining element may take various configurations. For example, a simple projection extending from the inner wall of the outer tube will suffice. In such case, it is necessary to insure that the inner tube can readily be reciprocated passed this restraining device while the tampon is being restrained. In a specific embodiment described herein the wall of the inner tube is provided with two axially extending slots for receiving two restraining element. In an alternative embodiment the restraining element is no more than a portion of the distal end of the outer tube having a constricted diameter which will retard the movement of the tampon but will allow the inner tube to pass through. Again, the construction of the inner tube may be modified to facilitate its passing through such a constricted area.

In accordance with the teachings of this invention, the inner tube is provided with a plurality of radially spaced ribs extending longitudinally along the inside surface thereof, said ribs terminating, at their proximal end, in bearing surfaces.

In use then, the tampon-applicator assembly is presented in the compacted state. The user places the assembly in the insertion position by simply gripping the gripping portion and reciprocating the inner tube away from the outer tube. The assembly is now in the insertion position with the tampon transferred into the proximal end of the outer tube end with the ribs of the inner tube directly behind the tampon so that the bearing surfaces at the proximal end of the ribs may bear against the distal end of the tampon. By simply pushing the inner tube toward her body the user can expel the tampon.

In a preferred embodiment, the tampon of the tampon-applicator assembly is of the kind illustrated in U.S. Pat. No. 2,798,260 issued on July 9, 1957 to F. Niepmann et al. This tampon is manufactured from a cylindrical blank of loosely associated absorbent materials. The blank is subjected to a radial compression step which by its nature produces a compressed cylindrical tampon having a plurality of radially spaced, longitudinally extending grooves in the tampon external surface. The ribs of the inner tube are adopted to fit within these grooves so that when the tampon-applicator is in the collapsed position, the tampon may reside within the inner tube without being unduly restricted by virtue of the ribs.

When placing this preferred tampon-applicator assembly into the insertion position, the inner tube is again reciprocated so that the ribs clear the distal end of the tampon. To bring the bearing ends of the ribs into bearing contact with the tampon, the inner tube is rotated slightly so that the ribs are out of register with the grooves of the tampon and so may be brought to bear against the distal end thereof. Provision must be made to allow the inner tube to so rotate. In a specific embodiment described herein, wherein the inner tube is provided with a slot for receiving a restraining element, the slot is of sufficient width to allow the inner tube to be rotated.

BRIEF DESCRIPTION OF THE DRAWINGS

FIG. 1 is an exploded, prospective view of the tampon-applicator assembly of this invention;

FIG. 2 is a longitudinal cross-sectional view of the assembly of FIG. 1 shown in the collapsed state and taken through the longitudinal axis thereof;

FIG. 3 is a cross-sectional view of the assembly shown in FIG. 2 taken through line 3—3;

FIG. 4 is a longitudinal cross-sectional view of the assembly of FIG. 1 shown in the insertion position and taken through the longitudinal axis thereof; and FIG. 5 is a cross-sectional view of the assembly shown in FIG. 4 and taken through line 5—5.

DETAILED DESCRIPTION OF THE INVENTION

Referring now to FIGS. 1 through 5 shown there is a tampon-applicator assembly 10 of this invention.

FIG. 1 illustrates, in exploded, prospective view, a major components of the assembly, namely, an inner tube 12 and an outer tube 14 and a catamenial tampon 16. The catamenial tampon 16 is provided with the usual withdrawal string 17. In the preferred embodiment illustrated in the drawings, the tampon is of the type illustrated in U.S. Pat. No. 2,798,260, i.e., a tampon made from a cylindrical blank which is compressed radially into a rigid cylinder having longitudinally extending grooves 19 in the external surface of the tampon. The assembly and its components are shown in the drawings with the proximal end on the reader's left and the distal end on the reader's right. Both the inner and outer tubes comprise thin walled cylinders, open at both ends and each only somewhat larger than the tampon 16 with respect to length and diameter. The inner tube 12 is of a sufficiently smaller diameter than the outer tube so as to be able to snugly nest within the outer tube in the configuration shown in FIGS. 2, 3 and 4. By snugly nesting, it is meant that the inner tube fits tightly enough to avoid unintended dislodging when the assembly is in the collapsed position as shown in FIG. 2 while, at the same time, is loose enough so as to be easily reciprocated into the tampon insertion position as shown in FIG. 4 and not offer untoward resistance when the tampon is being inserted from this position.

As is shown in FIG. 2, the inner tube 12 is nested within the outer tube 14 and the tampon 16 is enclosed within the inner tube. The tampon-applicator assembly in this configuration, which is the one presented to the user prior to use, is essentially no longer than the tampon 16 itself. The withdrawal string 17 is extended out of the distal end of the assembly so that the user can be assured that the string is firmly attached to the tampon prior to inserting the same.

The proximal end of the outer tube terminates in a set of petals 24. These petals are flexibly biased toward the axis of the tube and are adapted to present a smooth, domed leading surface to minimize user's discomfort during insertion.

The distal end of the inner tube 12 is provided with a gripping portion which extends out of the distal end of the outer tube 14 when the assembly is in the collasped state and is adapted to be gripped by the user to reciprocate the inner tube almost completely out of the outer tube and place the assembly into the insertion position shown in FIG. 4. In the embodiment illustrated, the gripping portion comprises a ring 20, circumscribing the extreme distal portion of the outer periphery of the inner tube 12. To make this ring accessible for gripping, a space projection 22 is provided on the outer wall of the inner tube to keep the ring spaced away from the outer tube 14.

By gripping the outer tube in one hand and the ring 20 of the inner tube in the other, the assembly may be placed into the insertion position shown in FIG. 4. In accordance with this invention, when the inner tube is so reciprocated means are provided for restraining the tampon 16 from reciprocating along with the inner tube 12. In the embodiment illustrated in FIGS. 1-4, these means comprise restraining elements 28 provide at the distal end of the outer tube to bear against the distal end of the tampon 16 and restrain the tampon from moving toward the distal end of the outer tube. Accordingly, as the inner tube is reciprocated out of the outer tube, the tampon is restrained and, in effect, is transferred from the inner tube to the outer tube.

In order to allow the inner tube 12 to pass by the restraining elements 28, slots 30 are provided extending longitudinally through the wall of the inner tube 12. The restraining elements 28 may then be fitted into slots 30 and hence the inner tube will be free to move relative thereto. Additionally, the combination of the restraining elements and the slots will prevent the inner tube from undesirable rotation. By having the slots fall short of the extreme end of petals 24, slot end surfaces 32 are provided which, in cooperation with restraining elements 28, will prevent the inner tube from unintentionally being reciprocated completely out of the outer tube.

As best illustrated in FIG. 1, the inner tube is provided with a plurality of radially spaced ribs 31 extending longitudinally along the inside surface thereof. The ribs terminate, at the proximal end of the inner tube in bearing surface 33. When in the collapsed state, the ribs 31 are adapted to fit within the grooves 19 of the tampon so that the tampon may reside within the inner tube without being unduly restricted by virtue of the presence of the ribs. This is best illustrated in FIG. 3 which shows, in radial cross-section, the assembly in the collapsed position with the ribs and grooves in register.

When the tampon-applicator assembly is placed into the insertion position as illustrated in FIG. 4, the inner tube has been reciprocated so that the ribs clear the distal end of the tampon. To bring the bearing surfaces 33 of the ribs into bearing contact with the tampon, the inner tube is rotated slightly so that the ribs are out of register with the grooves and may be brought to bear against the distal end of the tampon. In order to allow such rotation, the slot 30 in which restraining element 28 is engaged must be wide enough to provide sufficient play to allow rotation. The assembly in the insertion position and with the ribs out of register with the grooves is illustrated in FIG. 5 which is a radial cross-sectional view taken through line 5—5 of FIG. 4. The play or clearance require to allow such rotation is shown in FIG. 5 by the dimension C.

With the inner tube rotated so that the ribs bear against the distal end of the tampon, the user may reciprocate the inner tube in the proximal direction to eject the tampon.

The inner and outer tubes of the tampon-applicator assembly of this invention may be constructed of various materials, such as paper board, synthetic polymers or the like. Preferably, there constructed a moldable polymers with polypropolene or polyethylene being the materials of choice.

What is claimed is:

1. In a tampon applicator assembly having a proximal end, a distal end, and comprising a generally cylindrical outer tube; a generally cylindrical inner tube having an outside diameter less than the inside diameter of said outer tube, said inner tube being snugly nested, coaxially within said outer tube;

a tampon enclosed coaxially within said inner tube;

a gripping portion affixed to the distal end of said inner tube and extending out of the distal end of said outer tube for gripping said inner tube and reciprocating said tube almost completely out of said distal end of said outer tube;

and at least one restraining element in the distal half of the outer tube for restraining said tampon from reciprocating with said inner tube so that the tampon will remain enclosed by said outer tube when said inner tube is reciprocated;

the improvement wherein said inner tube is provided with a plurality of radially spaced ribs extending longitudinally along the inside surface thereof, said ribs terminating at the proximal ends thereof in bearing surfaces; whereby when said inner tube is reciprocated, said tampon will be transferred from said outer tube and when said reciprocated inner tube is then urged towards the proximal end of the assembly, the bearing surfaces of said ribs will bear against the distal end of said tampon and expel said tampon.

2. The tampon applicator assembly of claim 1 wherein said tampon is provided with a plurality of radially spaced longitudinally extending grooves adapted to engage the plurality of radially spaced ribs of the inner tube when said tampon is enclosed within said inner tube.

3. The tampon applicator assembly of claim 2 wherein means are provided for rotating the ribs out of alignment with said grooves when said inner tube is reciprocated almost out of said distal end of said outer tube.

4. The tampon applicator assembly of claim 3 wherein said restraining element comprises a projection extending from the inner wall of the outer tube and adapted to engage an axially extending slot provided in the wall of the inner tube; and means for rotating ribs out of alignment with said grooves comprising, providing said slot with sufficient clearance to allow such rotation.

* * * * *